United States Patent [19]

Nilsson et al.

[11] Patent Number: 5,683,980

[45] Date of Patent: Nov. 4, 1997

[54] USE OF IGF-BP FOR REFOLDING OF IGF

[75] Inventors: Björn Nilsson, Sollentun; Sophia Elisabeth Hober, Stockholm, both of Sweden

[73] Assignee: Pharmacia & Upjohn AB, Stockholm, Sweden

[21] Appl. No.: 646,365

[22] PCT Filed: Nov. 14, 1994

[86] PCT No.: PCT/SE94/01076

§ 371 Date: Aug. 5, 1996

§ 102(e) Date: Aug. 5, 1996

[87] PCT Pub. No.: WO95/14034

PCT Pub. Date: May 26, 1995

[30] Foreign Application Priority Data

Nov. 16, 1993 [SE] Sweden .................. 9303784

[51] Int. Cl.[6] .................. A61K 38/28; C07K 14/00
[52] U.S. Cl. .................. 514/3; 530/303
[58] Field of Search .................. 530/303; 514/3

[56] References Cited

U.S. PATENT DOCUMENTS 5,158,875 10/1992 Miller et al. .................. 435/69.1
5,407,913 4/1995 Sommer et al. .................. 514/121

FOREIGN PATENT DOCUMENTS 0 369 943    5/1990   European Pat. Off. .
WO 92/14834  10/1992  WIPO .
WO 93/11240  6/1993   WIPO .
WO 93/19084  10/1993  WIPO .

OTHER PUBLICATIONS

Biosci. Biotech. Biochem., vol. 56, No. 1, 1992, Yasamusa Marumoto et al, "Purification and Refolding of Recombinant Human IGF II from Silkworms Infected with Recombinant Bombyx mori Nuclear Polyhedrosis Virus" pp. 13–16.

Bio/Technology, vol. 9, Apr. 1991, Elisabet Samuelsson et al, "Facilitated In Vitro Refolding of Human Recombinant Insulin–Like Growth Factor I Using a Solubilizing Fusion Partner" pp. 363–366.

*Primary Examiner*—Cecilia J. Tsang
*Assistant Examiner*—Bennett Celsa
*Attorney, Agent, or Firm*—Dinsmore & Shohl LLP

[57] ABSTRACT

Processes for refolding of insulin-like growth factor (IGF) comprise contacting IGF in a reduced or misfolded form with insulin-like growth factor binding protein (IGF-BP), and recovering native IGF.

14 Claims, 3 Drawing Sheets

USE OF IGF-BP FOR REFOLDING OF IGF

This is a 371 of PCT/SE 94/01076 filed Nov. 14, 1994.

FIELD OF THE INVENTION

The present invention relates to the use of insulin-like growth factor binding protein (IGF-BP) for refolding of Insulin-like growth factor (IGF) and to a process for the production of biologically active and native IGF-I, characterised in that IGF-I in a reduced or misfolded form is subjected to treatment with IGF-BP to obtain disulphides bridges between cysteine residues 6–48, 18–61 and 47–52, respectively.

BACKGROUND OF THE INVENTION

Human insulin-like growth factor I (IGF-I) is a single-chain peptide growth factor of 70 amino acids, originally isolated from serum. IGF-I is positively regulated by growth hormone (GH) and shows mitogenic effects on many cell types. Therefore, IGF-I is thought to mediate many of the growth promoting effects of GH. In the regions of homology, IGF-I and insulin are 49% homologous, including the six cysteine residues, furnishing three disulphide bridges. The three dimensional structure of IGF-I has been modelled based on the x-ray structure of insulin, and this model has recently been confirmed in the disulphide bridge regions by distance constraints obtained by 2-D NMR spectroscopy of IGF-I (for a review on. IGF, see: Insulin-like growth factors I and II, Humbet R. E, Eur. J. Biochem 190, 445–462,1990).

Human recombinant IGF-I has been produced as a secreted product in both *Escherichia coli* and *Saccharomyces cerevisiae*. In isolated material from both species, IGF-I is found mainly as misfolded forms with intermolecular disulphides. Surprisingly, two distinct monomeric forms, with differences in theft disulphide bond patterns, have been identified. One of these two forms contains the disulphide bond topology expected from the insulin structure, and this form (disulphides 6–48, 47–52 and 18–61) is biologically active. The other monomeric form, designated 'mis-matched' (disulphides 6–47, 48–52 instead of the native 6–48, 47–52), lacks IGF-I receptor affinity. In addition, in vitro refolding of reduced IGF-I by oxygen, has demonstrated that native, mis-matched and aggregated IGF-I accumulate, even under dilute refolding conditions (Iwai, M., et al (1989) J. Biochem. Vol. 106, Page 949; Samuelsson, E., et al (1991) Bio/Technology Vol. 9, Page 363).

In serum, and in other body fluids, IGF-I, IGF-II, and variants of these two IGFs are often bound to specific carrier proteins which have been designated IGF binding proteins (IGF-BPs). To date, six distinct, but homologous, IGF-BPs have been characterised. There are a number of reports, some of them contradictory, concerning the biological significance of the different IGF-BPs; to protect IGFs from clearance and proteolytic degradation, to transport IGFs to different tissues, to play a part in hormone regulation, to prevent hypoglycaemia by inhibiting binding of IGF-I to the insulin receptor, to increase the potency of IGFs by interacting with cell surfaces, to remove IGFs from tissue and to inhibit the biological activity of IGFs (for a recent review on IGF-BPs, see Shimasaki and Ling (1992) Progress in Growth Factor Research, Vol. 3, Page 243).

An expression system for production of the complex between IGF and IGF-BP53, is disclosed in WO 89/09268 (Genentech). The host cell is a CHO-cell. The complex is proposed to be useful for metabolically affecting the circulatory system in mammals.

A major problem when recombinant proteins are over-produced in efficient bacterial expression systems is related to the folding of the protein products into their native conformations. Many high level expression system in *Escherichia coli* results in the production of aggregates of denatured proteins, so called inclusion bodies, which in some cases may be refolded into the wanted native protein. In this refolding process, the inclusion body must be dissolved e.g. with a denaturant, such as guanidine or urea. If needed, reduction of disulphide bonds are also performed. By dilution or dialysis, the protein can be refolded into its native three dimensional conformation. However, the yield of a refolding procedure is unpredictable since the protein product often aggregates or gets modified. In addition, for IGF-I and II, the soluble refolded fraction will contain misfolded species and the overall yield of correctly folded growth factor is rather low (Samuelsson, E., et al (1991) Bio/Technology Vol. 9, Page 363).

Methods to facilitate and render the refolding more effective have been described. One method is to use of a class of heat-shock-proteins (HSP) called chaperones and another is to utilize folding enzymes. By using HSP, aggregation may be avoided and by using the folding enzymes, the speed of refolding may be accelerated. However, not all protein are susceptible for these methods and other solutions to enhance refolding yields have been suggested. In an article by J D Carlson et al, in Biotechnology, Vol 10NO. 1, page 86, January 1992, the use of monoclonal antibodies during protein refolding, to enhance the yield of native protein, especially S-Protein, has been disclosed.

In order to increase the yield of correctly folded IGF different methods have been proposed.

The refolding yield of recombinant IGF-I was significantly improved by utilising a fused fusion partner, consisting of two IgG-binding domains (ZZ) derived from staphylococcal protein A (Samuelsson, E., et al (1991) Bio/Technology Vol. 9, Page 363). The ZZ fusion partner is used to solubilise misfolded molecules before, during and after reduction and reoxidation. The yield of correctly folded IGF-I is shown to be substantially increased but there is still a significant amount of misfolded IGF.

Patents and patent applications have also described the problem of misfolded IGF and suggested different improvements. WO 91/02807 (Amgen) (=U.S. Pat. No. 5158875) discloses a method for refolding IGF-I in the presence of a fused short positively charged leader sequence, in which amino acids such as lysine, arginine and histidine are fused at the N-terminus of IGF-I. In WO 93/11240 (Genentech) a method for refolding of insoluble and improperly folded IGF-I is described involving solubilisation and refolding in a single buffer system.

However, a method to quantitatively refold misfolded IGF into its native disulphide conformation is not yet described.

A biophysical explanation to this refolding problem has been described (Hober S et al (1992) Biochemistry Vol. 31, Page 1749). The folding problem for IGF-I is thermodynamic, and not kinetic as may be expected, and at least one of the three disulphide bridges (47–52) is energetically unfavourable in the native conformation.

SUMMARY OF THE INVENTION

This invention has solved the problem of getting native, correctly folded IGF in a higher mount in a process when IGF which is obtained in a reduced or misfolded state. Most surprisingly, we found that in the presence of Insulin-like Growth Factor Binding Protein 1 (IGF-BP-1), the native disulphides in IGF-I are quantitatively formed. These results demonstrate that IGF-BP act in vitro to guide the formation of correct disulphides in the IGF molecule.

Thus, the invention relates to the use of Insulin-like growth factor binding protein (IGF-BP) for refolding of Insulin-like growth factor, (IGF-I or IGF-II). The binding protein could be any of IGF-BP-1, IGF-BP-2, IGF-BP-3, IGF-BP-4, IGF-BP-5 and IGF-BP-6. The Insulin-like growth factor is preferably IGF-I and the binding protein is preferably IGF-BP-1. The relative mount of IGF and binding protein is preferably in equal molar mount.

The invention also relates to a process for the production of biologically active native IGF-I or IGF-II, characterised in that IGF-I or IGF-II in a reduced or misfolded form is subjected to treatment with IGF-BP, preferably IGF-BP-1. The relative mount of IGF and binding protein is preferably in equal molar mount.

The claimed process can be a treatment in vitro in which IGF-BP and IGF-I are mixed, preferably in the presence of a redox system, and thereafter recovering of the native IGF-I or IGF-II or a process for coexpression of IGF-I and the binding protein in an in vivo system in *E. coli* and thereafter recovering the native IGF-I or IGF-II. This coexpression is performed in order to accumulate the native, correctly folded IGF.

The process has been exemplified by IGF-I and IGF-BP-1, but for a person skilled in the art, this teaching can also be applied for IGF-II and other binding proteins as the binding proteins are all homologous (Shirnasaki and Ling (1992) Progress in Growth Factor Research, Vol. 3, Page 243).

BRIEF DESCRIPTION OF THE DRAWING

FIG. 2 A In a gluthatione redox buffer a in presence and b in absence of IGF-BP-1.

FIG. 2 B Air oxidation of reduced IGF-I in one hour c with and d without IGF-BP-1.

DETAILED DESCRIPTION

Preparation of the native mis-matched and reduced forms of IGF-I

Native and mis-matched IGF-I were produced in *E. coli* as fusion proteins and purified to homogeneity as described (Forsberg, G., et al (1990) Biochem. J. Vol. 271, Page 357). Reduced IGF-I was prepared by incubating a mixture of native and mis-matched IGF-I at 37° C. for 1 h at a concentration of 170 mM in a buffer containing 0.1M Tris, pH 8.7, 0.2M KCl, 1 mM EDTA, 8M Urea and 10 mM reduced dithiothreitol (DTT) (Hober S et al (1992) Biochemistry Vol. 31, Page 1749).

Preparation of IGF-BP-1

Recombinant IGF-BP-1 was purified from conditioned medium of DON cells expressing a human IGF-BP-1 gene. The gene was harboured on a Bovine Papilloma Viral vector. IGF-BP-1 was purified to homogeneity by IGF-I affinity chromatography and RP-HPLC.

Protein analysis

IGF-I concentrations were calculated from their absorbances at 280 um using the specific absorption constant $A_{280}$ (0.1%, 1 cm)=2,1. UV-absorbance spectra were determined in a Kontron 860 spectrophotometer (Kontron, Switzerland).

Disulphide exchange reactions of IGF-I

Disulphide exchange reactions were carried out for 1 hour at 37 ° C. at an IGF-I concentration of 30 mM in a buffer containing 0.1M Tris, pH 8.7, 0.2M KCl, 1 mM EDTA, 10 mM reduced glutathione (GSH) and 1 mM oxidized glutathione (GSSG). Disulphide exchanges were terminated by alkylating free thiols using 160 mM vinylpyridine (VP). The pyridylethylation reaction was allowed to proceed for 15 minutes in the dark whereafter the buffer was exchanged to 10 mM HCl using gel filtration on Sephadex G-25 (Pharmacia LKB Biotechnology, Sweden).

Separation of IGF-I variants and IGF-I peptide fragments

Pyridylethylated variants of IGF-I were separated by RP-HPLC. The column used was a Kromasil $C_8$ with 7 mm particles having a pore diameter of 18 um (Eka Nobel, Sweden). The gradient used was 30 to 45% acetonitrile in 0.25% pentafluoropropionic acid (PFPA) over 30 min, at a flow rate of 1 ml/min and a temperature of 30° C. The elution was monitored by a diode array detector and a fluorescence detector in series (Hewlett Packard, USA).

EXAMPLES

Folding of IGF-I in the presence of IGF-BP-1

Figure 1:
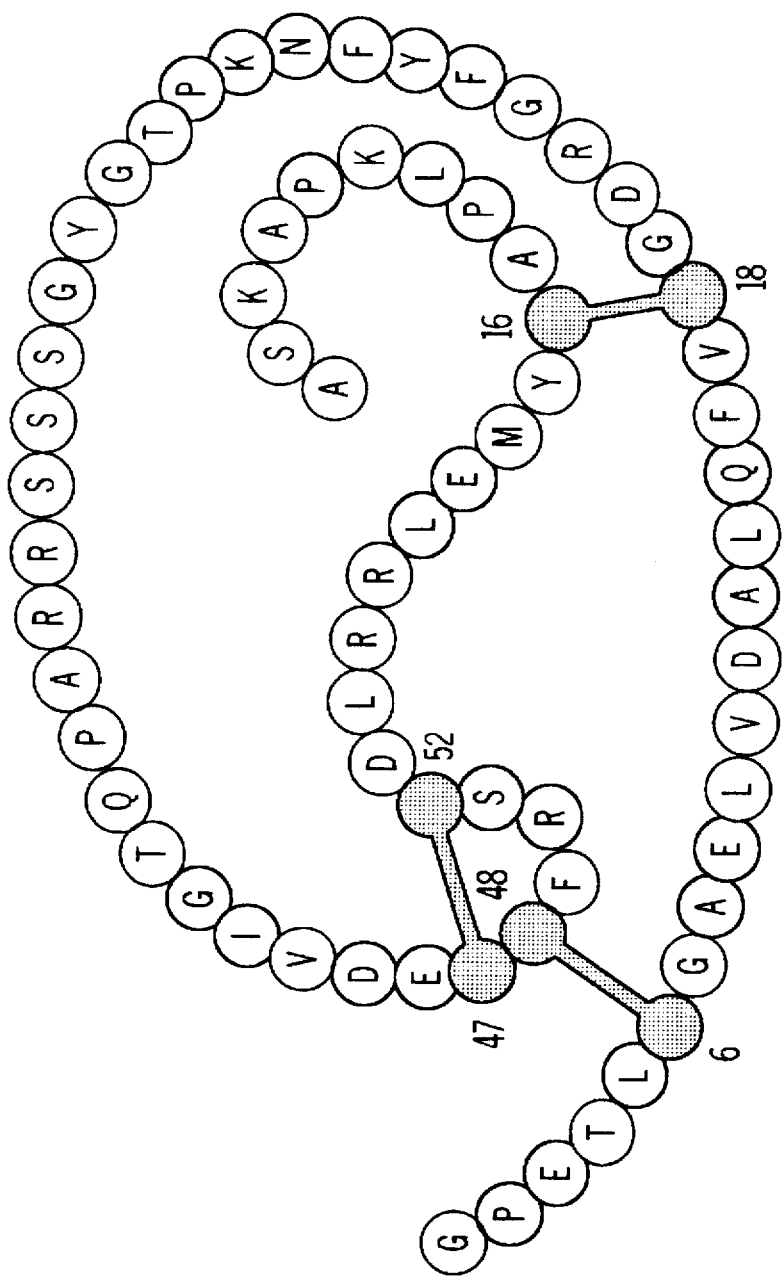
FIG. 1: A schematical representation of native IGF-I.
Figure 2A:
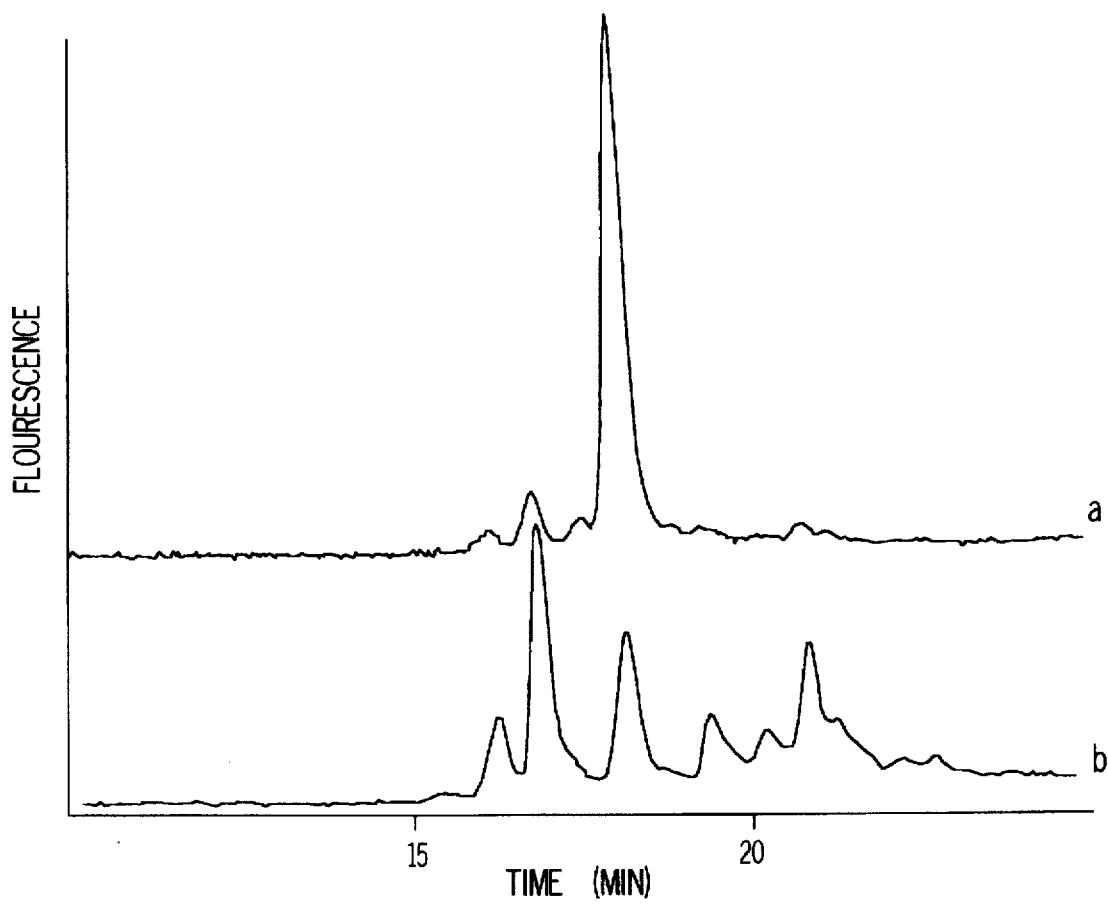
FIG. 2: RP-HPLC separation of different forms of IGF-I
Figure 2B:
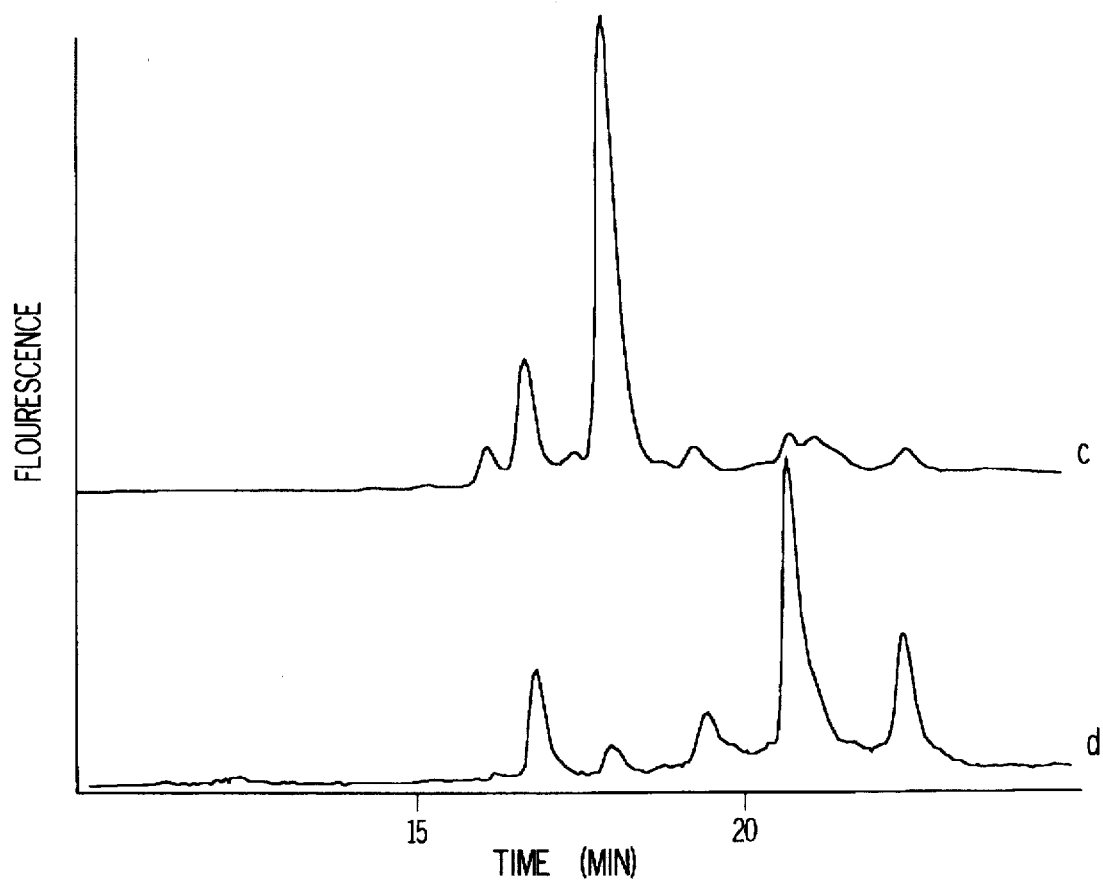

The ability of IGF-BP-1 to aid in the folding of IGF-I was studied in a glutathione buffer (oxidised gluthatione/reduced gluthatione; GSSG/GSH). Native, mismatched and reduced IGF-I, respectively, were folded in presence or absence of IGF-BP-1. After the refolding mixture had reached equilibrium (30 minutes), disulphide exchange reactions were terminated by alkylation of free thiols with vinyl pyridine. The different forms of IGF-I were separated on RP-HPLC as shown in FIGS. 2A and 2B. The fluorescence (excitation at 280 nm and emission at 305 nm) of the different peaks was measured. The chromatograms in FIG. 2A show samples from incubation of reduced IGF-I in a glutathione buffer in presence (a) and absence (b) of IGF-BP-1. The chromatograms in FIG. 2B show air oxidation of reduced IGF-I in one hour with (c) and without (d) IGF-BP-1.

In the GSSG/GSH buffer system and in the absence of IGF-BP-1, native IGF-I accounts for 22% of the total amount of IGF-I at equilibrium and the most populated specie only has two disulphide bridges (Hober S et al (1992) Biochemistry Vol. 31, Page 1749). However, in the presence of IGF-BP-1, in similar molar concentration as IGF-I, IGF-I attains its native conformation to 89% (Table 1, FIG. 2A, at appr 18 min). The relative amounts of the analysed different forms of IGF-I are shown in Table 1.

In order to study if IGF-BP-1 has a catalytic function in folding or if it acts by changing the equilibrium by its binding, we made the refolding experiment with 10x and 100x excess of IGF-I over IGF-BP-1 (Table 1). These results suggest that IGF-BP acts by shifting the folding equilibrium through binding and, thus, that equal molar amounts of IGF-BP and IGF-I are necessary to quantitatively generate the native form of IGF-I. As a control experiment albumin was added to the equilibrium mixture, and no effects on the disulphide exchange thermodynamics of IGF-I was observed (Table 1).

Refolding experiments were also performed in the presence and absence of IGF-BP-1, and utilising air oxygen as the oxidant. In the absence of IGF-BP-1, after one hour, several different forms of IGF-I were detected. These were mainly IGF-I with one or no disulphide bridge (FIG. 2B, d.). In contrast, when IGF-I was refolded in the presence of equal molar mount of IGF-I and IGF-BP, mainly the native form of IGF-I was found in the mixture (FIG. 2B, c, appr 18 min).

TABLE 1

Relative amounts of the different IGF-I conformations in presence and absence of IGF-BP-1 or albumin (control). The IGF-I protein concentration was 30 mM in all experiments. O is the reduced IGF-I, I is a one disulphide form, IIa and IIb are differfent forms containing two disulphides, III' is mismatched IGF-I and III is native IGF-I.

| start | GSSG/GSH | BP1 [µM] | Albumin [µM] | III' [%] | IIa [%] | III [%] | IIb [%] | I [%] | O [%] |
|---|---|---|---|---|---|---|---|---|---|
| O | 1/10 | 30 | 0 | <4 | 11 | 89 | <4 | <4 | <4 |
| O | 1/10 | 0 | 0 | 11 | 30 | 22 | 12 | 25 | <4 |
| O | 1/10 | 0 | 30 | 10 | 30 | 23 | 11 | 26 | <4 |
| O | — | 30 | 0 | 4.5 | 15 | 56 | 5.5 | 15 | 4 |
| O | — | 0 | 0 | <4 | 12 | 4 | 12.5 | 50 | 21.5 |
| III' | 1/10 | 30 | 0 | 5 | 11 | 94 | <4 | <4 | <4 |
| III' | 1/10 | 0 | 0 | 10 | 31 | 72 | 12 | 25 | <4 |
| III | 1/10 | 30 | 0 | 4 | 10 | 96 | <4 | <4 | <4 |
| III | 1/10 | 3 | 0 | 9 | 30 | 9 | 8 | 24 | <4 |
| III | 1/10 | 0.3 | 0 | 11 | 32 | 26 | 8 | 23 | <4 |
| III | 1/10 | 0 | 0 | 10 | 32 | 22 | 9 | 27 | <4 |

Thus, we have demonstrated that the described thermodynamic folding problem of IGF-I is solved by IGF-BP-1. In the equilibrium experiments, there are as much as 84% to 89% (Table 1) native IGF-I when the redox reaction is allowed to proceed in the presence of IGF-BP-1. Oxidation of reduced IGF-I with oxygen together with IGF-BP-1 is both faster and more selective than oxygen oxidation without binding protein-1 (Table 1).

We claim:

1. A process for refolding of Insulin-like growth factor (IGF), comprising contacting IGF in a reduced or misfolded form with Insulin-like growth factor binding protein (IGF-BP), and recovering native IGF.

2. A process according to claim 1, wherein the binding protein is any of IGF-BP-1, IGF-BP-2, IGF-BP-3, IGF-BP-4, IGF-BP-5, and IGF-BP-6.

3. A process according to claim 1, wherein the Insulin-like growth factor is IGF-I.

4. A process according to claim 2, wherein the Insulin-like growth factor is IGF-I.

5. A process according to claim 1 whereby the binding protein is IGF-BP-1.

6. A process according to claim 2, whereby the binding protein is IGF-BP-1.

7. A process according to claim 1, wherein the binding protein and IGF are employed in equal molar amounts.

8. A process according to claim 2, wherein the binding protein is employed in equal molar amount to that of IGF.

9. A process according to claim 1, wherein the contacting step is in vitro, and wherein IGF-BP and IGF-I are admixed and thereafter the native IGF-I is recovered.

10. A process according to claim 5, wherein the contacting step is in vitro, and wherein IGF-BP and IGF-I are admixed and thereafter the native IGF-I is recovered.

11. A process according to claim 9, wherein the IGF-BP and IGF-I are admixed in the presence of a redox system.

12. A process according to claim 10, wherein the IGF-BP and IGF-I are admixed in the presence of a redox system.

13. A process according to claim 9, wherein the binding protein and IGF are employed in equal molar amounts.

14. A process according to claim 10, wherein the binding protein and IGF are employed in equal molar mounts.

* * * * *